US010279079B2

(12) United States Patent
Davis et al.

(10) Patent No.: US 10,279,079 B2
(45) Date of Patent: May 7, 2019

(54) COMPOSITIONS AND METHODS FOR SPINAL DISC REPAIR AND OTHER SURGICAL AND NON-SURGICAL INDICATIONS

(75) Inventors: Raphael Davis, Port Jefferson, NY (US); Divya Bhatnagar, Stony Brook, NY (US); Miriam Rafailovich, Plainview, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 387 days.

(21) Appl. No.: 14/129,988

(22) PCT Filed: Jul. 5, 2012

(86) PCT No.: PCT/US2012/045500
§ 371 (c)(1),
(2), (4) Date: May 27, 2014

(87) PCT Pub. No.: WO2013/006671
PCT Pub. Date: Jan. 10, 2013

(65) Prior Publication Data
US 2014/0294770 A1    Oct. 2, 2014

Related U.S. Application Data

(60) Provisional application No. 61/504,506, filed on Jul. 5, 2011.

(51) Int. Cl.
*A61L 27/48* (2006.01)
*A61L 27/18* (2006.01)
*A61L 27/26* (2006.01)
*A61L 27/38* (2006.01)
*A61L 27/52* (2006.01)
*A61L 27/54* (2006.01)
*C12N 5/077* (2010.01)

(52) U.S. Cl.
CPC .............. *A61L 27/48* (2013.01); *A61L 27/18* (2013.01); *A61L 27/26* (2013.01); *A61L 27/3834* (2013.01); *A61L 27/52* (2013.01); *A61L 27/54* (2013.01); *C12N 5/0656* (2013.01); *A61L 2400/06* (2013.01); *A61L 2430/38* (2013.01)

(58) Field of Classification Search
None
See application file for complete search history.

(56) References Cited

U.S. PATENT DOCUMENTS 3,579,465 A * 5/1971 Schmolka .............. A61K 8/042
424/60
6,040,295 A * 3/2000 Rolland ................ A61K 9/0019
514/44 R 2003/0206910 A1 * 11/2003 Nicol ..................... A61K 39/00
424/178.1
2005/0113923 A1   5/2005 Acker et al.
2009/0012627 A1   1/2009 Claesson et al.
2009/0157017 A1   6/2009 Ambrosio et al.
2009/0214685 A1   8/2009 Hunt
2009/0311190 A1 * 12/2009 Gracias ................ A61K 9/0097
424/9.3
2010/0055184 A1   3/2010 Zeitels et al.

FOREIGN PATENT DOCUMENTS

| EP | 0938903 A1 * | 9/1999 | ........... A61K 9/0048 |
|---|---|---|---|
| WO | 1998/026797 | 6/1998 | |
| WO | 2002/044276 | 6/2002 | |
| WO | 2003/043576 | 5/2003 | |
| WO | 2004/022603 | 3/2004 | |
| WO | WO2004022603 | 3/2004 | |
| WO | 2005034800 A2 | 4/2005 | |
| WO | 2005034800 A3 | 4/2005 | |
| WO | 2006/014067 | 2/2006 | |
| WO | WO2006014067 | 2/2006 | |

OTHER PUBLICATIONS

Mayol et al., Euro. J. Pharma. Biopharma., 70:199-206 (2008).*
Lee et al., Soft Matter, 6:977-983 (2010).*
Olea et al., J. Chil. Chem. Soc., 59(2):2451-2454 (2014).*
Sun et al., J. Nanomedic. Nanotechnol., 2(5):1-6 (2011).*
Arutyunyan et al., Eur. Phys. J. B, 75:163-166 (2010).*
Natu et al., Biomed. Mater., 2:241-249 (2007).*
Chen et al., J. Pharma. Sci., 100(2):655-666 (2011).*
Kim et al., J. Controlled Release, 80: 69-77 (2002).*
Oh et al., Biomed. Mater. Res., 72A: 306-316 (2005).*
Gutowska et al., Anatom. Rec., 263:342-349 (2001).*
Rapoport et al (J. Pharam. Sci., 91(1):157-170 (2002).*
Kim et al., Macromol. Res., 18(4):387-391 (2010) (Year: 2010).*
Roy, S. et al., "Thermoreversible Gel Formulations Containing Sodium Lauryl Sulfate or n-Lauroylsarcosine as Potential Topical Microbicides against Sexually Transmitted Diseases," Antimicrob Agents Chemother, vol. 45, pp. 1671-1681, 2001.
Jung et al., "Preparation of TGF-β1-conjugated biodegradable pluronic F127 hydrogel and its application with adipose-derived stem cells," *Journal of Controlled Release* 147(1):84-91, 2010.
Lee et al., "Intradiscal drug delivery system for the treatment of low back pain," *Journal of Biomedical Materials Research Part A* 92(1):378-385, 2010.

(Continued)

*Primary Examiner* — Thomas J. Visone

(74) *Attorney, Agent, or Firm* — Hoffmann & Baron, LLP

(57) ABSTRACT

The present invention features, inter alia, biocompatible compositions that include a poloxamer and one or more additives such as hyaluronic acid, gelatin, fibronectin, or a peptide fragment of fibronectin. The compositions are useful in tissue repair or remodeling, including repair of an injured spinal disc, in drug delivery, in cell culture, and in inhibiting the formation of adhesions.

19 Claims, 3 Drawing Sheets

(56) References Cited

OTHER PUBLICATIONS

Lee et al., "Thermo-sensitive, injectable, and tissue adhesive sol-gel transition hyaluronic acid/pluronic composite hydrogels prepared from bio-inspired catechol-thiol reaction," *Soft Matter* 6:977-983, 2010.
Roy et al., "Thermoreversible gel formulations containing sodium lauryl sulfate or n-lauroylsarcosine as potential topical microbicides against sexually transmitted diseases," *Antimicrob Agents Chemother* 45:1671-1681, 2001.
Tan et al., "Injectable, biodegradable hydrogels for tissue engineering applications," *Materials* 3:1746-1767, 2010.
Zhang et al., "Fabrication of gelatin-hyaluronic acid hybrid scaffolds with tunable porous structures for soft tissue engineering," *International Journal of Biological Macromolecules* 48:474-481, 2011.

* cited by examiner

COMPOSITIONS AND METHODS FOR SPINAL DISC REPAIR AND OTHER SURGICAL AND NON-SURGICAL INDICATIONS

CROSS-REFERENCE TO RELATED APPLICATIONS

This application is a U.S. national phase application of the international application PCT/US2012/045500, filed Jul. 5, 2012, which claims the benefit of the filing date of U.S. Provisional Application No. 61/504,506, filed Jul. 5, 2011. The content of that earlier-filed provisional application is hereby incorporated by reference herein in its entirety.

STATEMENT REGARDING FEDERALLY FUNDED RESEARCH

This invention was made with government support under grant number DMR0606387 awarded by the National Science Foundation. The government has certain rights in the invention.

FIELD OF THE INVENTION

The present invention relates to biocompatible materials that include a poloxamer, hyaluronic acid (HA), and/or gelatin. The materials are useful in various clinical and non-clinical situations, including spinal disc repair, drug delivery, and cell culture.

BACKGROUND

When a spinal disc becomes damaged due to trauma or disease, it may become necessary to replace the natural disc with a prosthesis. Such prostheses should preferably mimic the natural disc in shape and function, and several types of prostheses have been proposed. For example, Bao et al. disclosed a prosthetic spinal disc nucleus made of a hydrogel material that is implanted into an intradiscal space while the implant is dehydrated (U.S. Pat. No. 5,047,055). After the prosthesis is inserted, the hydrogel is hydrated and expands to a shape conforming to or approximating the natural nucleus. Bao et al. has also described a prosthetic nucleus having either a solid hydrogel core or a plurality of hydrogel beads surrounded by a membrane (U.S. Pat. No. 5,192,326). The prosthesis is implanted and hydrated to fill the intradiscal space. These devices rely on the natural annulus—fibrous tissue around the periphery of the natural disc—to constrain the expanded hydrogel. This essentially uncontrolled expansion creates a lateral force that acts directly on the annulus, which is typically already damaged. The additional force placed on the annulus by the prosthesis may impede healing and even cause further deterioration. In addition, it is difficult to accurately position dehydrated implants within the nucleus cavity.

Ray et al. disclosed one solution to the problems encountered by the prostheses of Bao et al. by proposing a hydrogel in a constraining jacket that expands on hydration (U.S. Pat. No. 6,602,291). Such a device is inserted into the intradiscal space in a first shape and is hydrated after insertion to assume a second shape that fills a volume less than the volume of the intradiscal space. This prosthesis may, however, still be difficult to implant properly. In addition, preparing the prosthesis outside of the patient may also create problems and requires the surgical team to make precise measurements of the implant site prior to inserting the prosthesis.

To provide improved prostheses, others have proposed a flow-able material that forms the prosthetic device. For example, Felt et al. disclosed an implant comprising a container that is inserted into the site of implantation and that is filled with a curable material, which is then cured in situ (U.S. Pat. No. 6,443,988). The shape of this implant may be manipulated in situ and its implantation is not hindered by a large size or awkward shape. Another flow-able prosthetic nuclear disc pulposus is disclosed by Milner et al. (U.S. Pat. No. 6,187,048). This implant comprises acrylates that are inserted into the intradiscal space and then induced to at least partially polymerize through the addition of a cross-linking agent. This prosthesis, however, is similar in composition to joint implants, which eventually decompose and may become mobile.

Another approach to the creation of a prosthesis that hardens in situ is disclosed by Ross et al. (U.S. Pat. No. 6,264,659). This implant is created by heating a thermoplastic material such as gutta percha to a temperature at which it becomes flow-able. The thermoplastic material is then injected into the intradiscal space and allowed to cool, thereby forming a prosthetic spinal disc nucleus. Implants such as these, however, utilize both polymers and/or additional curing agents that must be either mixed just prior to insertion or inserted separately. Still further, these implants may not be easily reversible.

SUMMARY

The present invention is based, in part, on our work with hyaluronic acid (HA)-gelatin-containing poloxamer hydrogels and our discovery of the manner in which including HA and gelatin varies the properties (e.g., stiffness) of the resulting hydrogel. The present compositions can mimic a natural spinal disc (or a certain property or properties thereof) and can also be used as delivery vehicles for cell-based therapeutics, biologics (e.g., therapeutic antibodies or antigens, such as microbial antigens delivered for the purpose of vaccination), and more traditional pharmaceutical agents (e.g., small organic compounds). The compositions are also useful in cell culture, allowing cell and/or tissue growth to be studied in three-dimensional matrices of varying stiffness. The biocompatible compositions that consist of, or that include, HA-gelatin-containing poloxamer hydrogels are liquid at low temperatures (e.g. between about 4° C. and about room temperature) and transition to a gel/solid phase at higher temperatures, including body temperature. As a result, they are easily injected into a patient where they subsequently gel. Suitable poloxamers, such as the copolymer present in aqueous solutions of Pluronic® F-127, are in a unimer state at the lower temperatures since both blocks (PEO and PPO) are water soluble at low temperatures. While the invention is not so limited, increasing the temperature is thought to cause the formation of spherical micelles with a core of mainly hydrophobic PPO blocks and a water-swollen corona of hydrophilic PEO blocks. It has been previously shown that at high concentrations, the micelles organize into a cubic structure and ordered micelle structures form due to repulsive interactions among closely packed spherical micelles. Hence, the material can be described as a micelle gel, as opposed to a chemical gel where the components are linked by covalent bonds. In our work, we added hyaluronic acid and/or gelatin polymer chains to form biocompatible, thermoreversible hydrogels with stiffness characteristics differing from those of hydrogels containing the corresponding poloxamer alone. As gelatin increases cell adhesion, migration, proliferation, and differentiation, it may be included when such activities are desired and omitted when they are not. The data we have generated so far indicate that compositions including HA and a poloxamer and excluding gelatin do not promote cell attachment. Other useful additives include fibronectin and polypeptide fragments of fibronectin, which we also believe promote cell adhesion.

Accordingly, in a first aspect, the invention features biocompatible compositions that include a poloxamer and one or more additives, the additive being hyaluronic acid, gelatin, fibronectin, a peptide fragment of fibronectin, or any combination thereof. As noted, the poloxamer includes polyoxypropylene (having a molar mass of about 1,000 to about 3,500 g/mol) and polyoxyethylene, and the composition can transition from a liquid at cooler temperatures (e.g., about 4° C.) to a gel at warmer temperatures (e.g., about 37° C.).

In any instance where we state that a composition "includes" certain components, it can include those components and other agents or it can include only those components; the compositions of the invention can comprise or can consist of the recited components. In one embodiment, the biocompatible compositions can include a poloxamer, as described herein, and hyaluronic acid. In another embodiment, the biocompatible compositions can include the poloxamer and gelatin. In another embodiment, the biocompatible compositions can include the poloxamer, HA, and gelatin. In another embodiment, the biocompatible compositions can include the poloxamer and fibronectin and/or polypeptide fragments of fibronectin (e.g., one or more distinct fragments that promote cell adhesion). In another embodiment, the biocompatible compositions can include the poloxamer, HA, and fibronectin and/or a polypeptide fragment thereof. In another embodiment, the biocompatible compositions can include the poloxamer, HA, gelatin, and fibronectin and/or a polypeptide fragment thereof.

In any of the various compositions, the poloxamer can be included in an aqueous solution containing about 20-40% poloxamer (w/v; e.g., about 25%, 30%, or 35% poloxamer); the HA can be included in an aqueous solution containing about 0.2-1.0% hyaluronic acid (w/v; e.g., about 0.4%, 0.5%, 0.6%, 0.7%, or 0.8% HA); and the gelatin can be included in an aqueous solution containing about 0.2-1.0% gelatin (w/v; e.g., about 0.4%, 0.5%, 0.6%, 0.7%, or 0.8% gelatin). For example, the biocompatible composition can include a mixture of a solution containing about 20-40% poloxamer (w/v), a solution containing about 0.2-1.0% hyaluronic acid (w/v), and a solution containing about 0.2-1.0% gelatin (w/v).

Where both HA and gelatin are included, solutions containing the respective additives can be mixed in roughly equal parts. For example, the biocompatible composition can include a solution of hyaluronic acid and a solution of gelatin mixed in a ratio of about 1:1 (HA:gelatin, v:v). For example, one can prepare a solution of about 0.5% HA and a solution of about 0.5% gelatin and then mix those solutions in a ratio of about 1:1 (v/v) and incorporate the mixed solution into the biocompatible compositions. For example, the compositions can include (a) a solution in which HA and gelatin have been mixed (e.g., in the amounts and manner as just described) and (b) a solution containing a poloxamer (e.g., about 30% w/v poloxamer). The solution containing HA, gelatin, or HA and gelatin can be mixed with the solution containing the poloxamer in a ratio of about 1:2 (v:v) to about 1:100 (v:v) (HA:poloxamer; gelatin:poloxamer; or HA-gelatin:poloxamer). For example, the solution of hyaluronic acid and gelatin can be mixed with the solution of poloxamer in a ratio of about 1:5 (v:v). To increase the stiffness of the resulting gel, the amount of poloxamer relative to the amount of HA can be increased. For example, the solution of hyaluronic acid and gelatin can be mixed with the solution of poloxamer in a ratio of about 1:10-1:20 (v:v) or of about 1:30, 1:40, 1:50, 1:60, 1:70, 1:80 (v:v) or ratios therein between.

The sources of the materials described above and elsewhere herein can vary. For example, the gelatin, HA, and fibronectin can be obtained from a mammalian source (e.g., a human, bovine, equine, or porcine source).

As noted, the poloxamer can include polyoxyethylene, which may be polypropylene glycol or polypropylene oxide (polypropylene glycol is generally understood to have a low to medium range molar mass and an end group, typically a hydroxyl group, that affects the properties of the polymer). The poloxomer can include a central hydrophobic chain of polyoxypropylene and two hydrophilic chains of polyoxyethylene. The poloxamer and the additive(s) may not be chemically cross-linked, and the compositions can be free from chemical cross-linking agents. In other embodiments, the poloxamer includes polypropylene glycol rather than, or in addition to, polypropylene oxide.

In any configuration, the compositions can include a detectable label to help position the composition as an implant in a desired area or to monitor the resulting implant over time. For example, the compositions can include a dye visible to the naked eye. Other markers, which may be used but are likely to be less convenient, include fluorescent compounds and low-energy radioisotopes.

In any configuration, the compositions can include a therapeutic agent. The agent can vary widely and can be an organic compound, including those currently known and prescribed for a wide variety of maladies, a nucleic acid, a polypeptide (naturally or non-naturally occurring), a multimeric protein (including antibodies and fusion proteins or conjugates) or a type of or mixture of biological cell (e.g., a stem cell or a progenitor cell that is not fully differentiated). Fully differentiated cells can be administered or studied as well with the present compositions.

In another aspect, the invention features methods of making the biocompatible compositions described herein. These methods can include a step of providing a solution that includes a poloxamer, wherein the poloxamer constitutes about 20-40% of the solution (w/v; any of the particular percentage amounts described herein can be used); a step of providing a solution comprising hyaluronic acid, wherein the hyaluronic acid constitutes about 0.2-1.0% of the solution (w/v; any of the particular percentage amounts described herein can be used); a step of providing a solution comprising gelatin, wherein the gelatin constitutes about 0.2-1.0% of the solution (w/v; any of the particular percentage amounts described herein can be used); a step of mixing the solution comprising hyaluronic acid with the solution comprising gelatin in a ratio of about 1:1 (v:v), thereby generating an HA-gelatin solution; and a step of mixing the HA-gelatin solution with the solution comprising the poloxamer in a ratio of about 1:2 to about 1:100 (HA-gelatin: poloxamer, v:v). The solvent can be an aqueous solvent, such as water. Biocompatible compositions made by such production methods are also within the scope of the present invention. The compositions can be sterilized. As noted, the compositions can include either HA or gelatin, and one of ordinary skill in the art would understand that where one or the other of these components are omitted, the step in the method described above in which they are provided would consequently be omitted.

In another aspect, the invention features kits that include one or more of the biocompatible compositions described herein and instructions for use (e.g., use as a spinal disc prosthesis, as a delivery device for a therapeutic agent, or as a cell culture medium). For example, the kit can include a composition of the present invention in solution or in a lyophilized or powdered form and instructions for use. Such kits can also include one or more additional components useful for culturing cells, such as media in solution or in a lyophilized or powdered form suitable for resuspension. Ancillary components such as containers (e.g., sterile, stoppered containers, such as a vial or tube), syringes, needles, gloves, and tubing, can also be included depending on the desired use.

The present hydrogels may have one or more of the following advantages. They may have one or more properties (e.g., a degree of stiffness) that are similar to the corresponding property (or properties) of a natural spinal disc; they may not require additive curing or cross-linking agents; and they may be implanted through a minimally invasive procedure. Other features and potential advantages are described in the detailed description, the examples, and the claims.

DETAILED DESCRIPTION

The present invention features both compositions of matter and methods of using them. Among the compositions are those including a poloxamer and at least one additive that modifies the stiffness of a gel formed by the composition relative to the stiffness of a gel formed from a comparable preparation lacking the additive. Poloxamers are generally understood to include polyoxypropylene (or polypropylene glycol) and polyoxyethylene, and such poloxamers can be incorporated in the present compositions. For example, the biocompatible compositions can include a block copolymer of ethylene oxide and propylene oxide. More specifically, the poloxamer can constitute a nonionic triblock copolymer containing a central hydrophobic chain of polyoxypropylene (poly(propylene oxide)) flanked by two hydrophilic chains of polyoxyethylene. The length of the chains can be varied, as can the amount of polyoxyethylene included (suitable molecular weights and other details are described further below).

Figure 3:
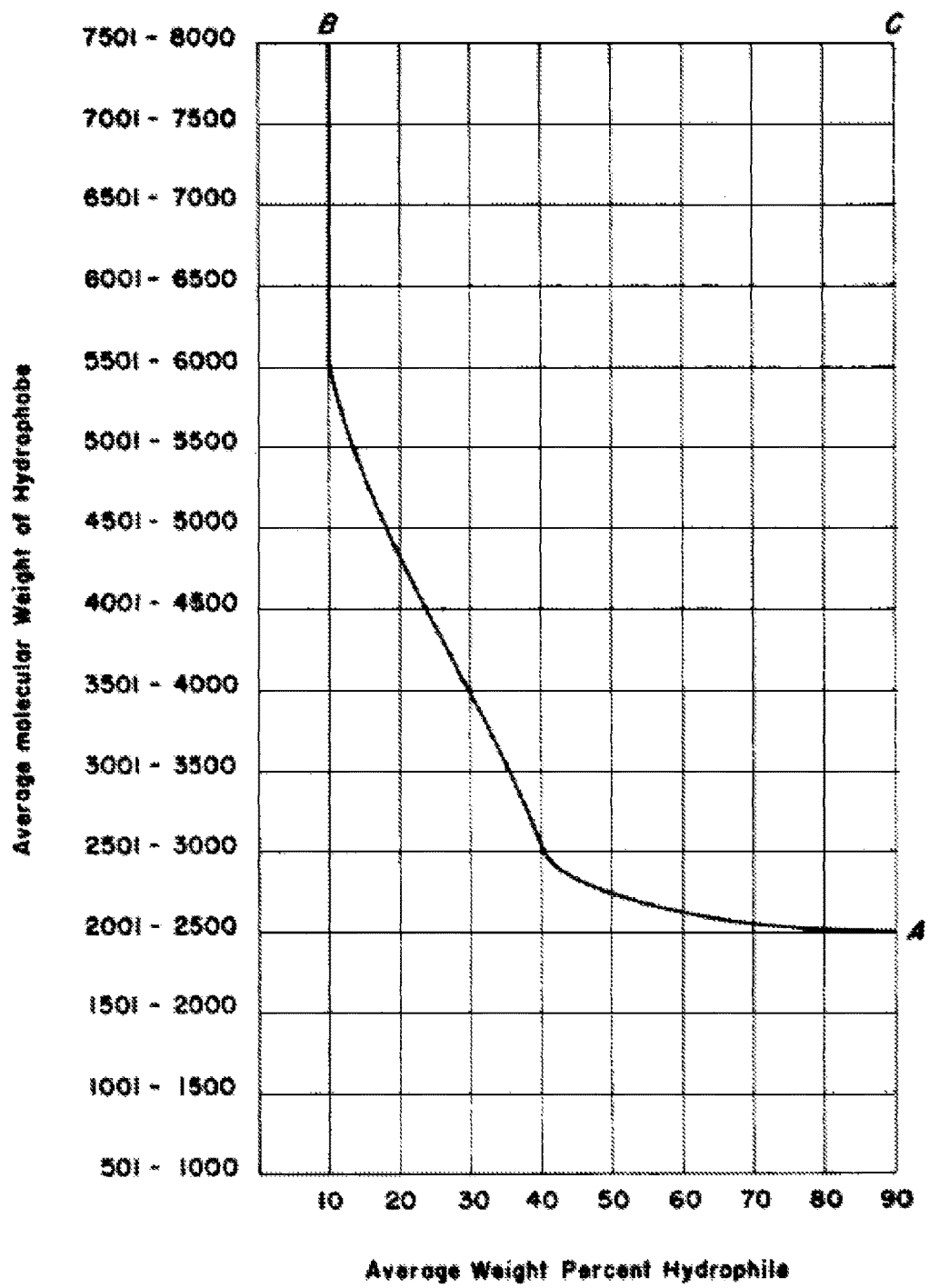
FIG. 3 is a graph with a curve for the "Average Molecular Weight of Hydrophobe" versus the "Average Weight Percent Hydrophile."

The poloxamer incorporated into the present compositions can be one that is commercially available (e.g., a Pluronic™ solution, gel, or solid, such as Pluronic™ F-127). Alternatively, the poloxamer can be made from raw materials according to methods known in the art (see, for example, U.S. Pat. Nos. 3,579,465 and 3,740,421, which are hereby incorporated by reference herein in their entirety). It is known that, within specific limits, aqueous solutions of polyoxyethylated polyoxypropylene glycol adducts of ethylene diamine will form gels (U.S. Pat. No. 3,579,465). These gels can include from about 20 to 90 weight percent of a polyoxyethylated polyoxypropylene glycol adduct of ethylene diamine and from 80 to 10 weight percent of an aqueous solvent such as water. The polyoxyethylated polyoxypropylene glycol adducts of ethylene diamine which may be employed in the preparation of the gels of the present invention may be represented by the following Formula I:

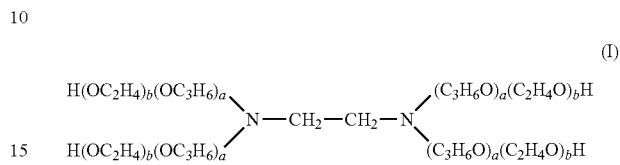

wherein a and b are integers such that the molecular weight of the hydrophobe and the weight percent of the hydrophile fall within the area ABC of the graph shown in FIG. 3. The polymers may have (1) a hydrophobe molecular weight of from about 2000 to about 8000, (2) a hydrophile content of from 10% to 90% by weight, and (3) a total molecular weight of from about 4000 to 100,000 (U.S. Pat. No. 3,579,465).

It is to be understood that by the term hydrophobe is meant the polyoxypropylene glycol adducts of ethylene diamine. As used herein, the term gel is defined as a solid or semisolid colloid containing considerable quantities of liquid. The particles in a gel are linked in a coherent meshwork which immobilizes the liquid. A colloidal solution with water as the dispersion medium is called, more specifically, a hydrosol. The gels within the scope of the present invention are more specifically ringing gels and may be described as gels that have a firm jelly-like consistency; that is, by tapping the gel lightly it will vibrate and return to its original configuration.

The hydrophobe base of the polymers of Formula I above is prepared by adding propylene oxide to the four hydroxyl groups of ethylene diamine. To be useful in the present invention, the hydrophobe base must have a molecular weight of at least about 2,000, preferably from 4,500 to 7,000. By adding ethylene oxide to the hydrophobe base, it is possible to put polyoxyetlrylene hydrophile groups on the ends of the molecule. These hydrophile poly oxyethylene groups may be controlled to constitute anywhere from 10% to 90% by weight of the polymer.

Because of the nature of aqueous solutions of the block polymers employed in the present invention, certain critical variables must be recognized in the preparation of gels therefrom. These variables are:

(1) the molecular weight of the hydrophobe base, (2) the weight percent of the hydrophile portion of the polymer, and (3) the weight percent concentration of block polymer in the gel. Only those polymers that have a hydrophobe molecular weight and a hydrophile percent weight falling within the area ABC of the graph shown in the figure are useful in the preparation of the ringing gels of the present invention. As demonstrated hereinafter, polymers falling outside of the area do not form gels regardless of the concentration of polymer in the gel.

Useful poloxamer gels can be prepared by dissolving from about 20% to about 90% (e.g., about 20-50%), by weight, of the block polymer, depending upon the molecular weight of the particular hydrophobe base used and the ethylene oxide content, in from about 80% to 10% (e.g., about 80-50%) cold water. The water should be at a temperature below at least 50° F. and preferably between 35° F. and 45° F. The block polymer is thoroughly mixed until it is dissolved in the water. The solution is then allowed to warm to room temperature, whereby a clear ringing gel is formed. As the temperature of the solution rises, it is believed that the hydrophile is partially dehydrated and micellar aggregation increases. It is surmised that formation of larger aggregates by the higher molecular weight hydrophobes entrap additional water as compared to the lower weight hydrophobes, this leading in turn to gel formation as the temperature increases. The gel, the stiffness of which can be altered by an additive, such as hyaluronic acid, forms at or above room temperature (e.g., physiological/body temperature).

It has been discovered that within specific limits aqueous solutions of oxyethylated-polyoxypropylene glycols will form gels. Thus, the gels of this invention comprise from about to 90 weight percent of a polyoxyethylatedpolyoxypropylene glycol wherein, for the purposes of this invention, the polyoxypropylene glycol hydrophobe has a molecular weight greater than 2,250 and to which has been added from about 16 to 360 moles of ethylene oxide. The balance of the composition is water. The polyoxyethylene-polyoxypropylene block polymer can be represented by the following Formula II:

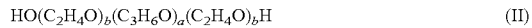

$$HO(C_2H_4O)_b(C_3H_6O)_a(C_2H_4O)_bH \quad (II)$$

wherein a is an integer such that the hydrophobe base represented by $(C_3H_6O)$ has a molecular weight of at least 2,250 and b is an integer from about 8 to 180 or more. When the hydrophobe has a molecular weight of 2,250, the gel contains at least 40% by weight of the block polymer and b is at least 26. When the hydrophobe has a molecular weight of 4,000, the gel contains at least 20% by weight of the block polymer and b is at least 136.

The hydrophobe base of the polyoxyethylene-polyoxypropylene block polymers of Formula II above is prepared by adding propylene oxide to the two hydroxyl groups of a propylene glycol nucleus. The hydrophobe base can be made to any controlled size. By adding ethylene oxide to the hydrophobe base, it is possible to put polyethylene oxide hydrophilic groups on both ends of the molecule. These hydrophilic ethylene oxide groups may be controlled to constitute anywhere from 10 to 90% of the final molecule. Not all of the block polymers of Formula II can be used. Because of the nature of aqueous solutions of this block polymer, three variables effect the formation of the gels. Therefore, it is necessary to recognize certain minimums for the three variables. These variables are:

(1) weight percent concentration of block polymer in the gel, (2) the molecular weight of the hydrophobic base $(C_3H_6O)$, and (3) the number of moles of ethylene oxide condensed on the hydrophobic base.

These minimums define a minimum weight percent concentration of the block polymer with a specific molecular weight polyoxypropylene hydrophobic base having a minimum number of moles of ethylene oxide condensed thereto necessary to form the ringing gels. Thus, at the minimum concentration with a specific molecular weight hydrophobic base, a minimum number of moles of ethylene oxide are required before the specific block polymer will form a gel in an aqueous solution.

The minimum weight percent concentrations with specific molecular weight hydrophobic base are set out below in Table I.

TABLE I

| M.W. of hydrophobic base | Min. weight percent concentration to form a gel | Min. number of moles of ethylene oxide required | Total M.W. of block polymer |
|---|---|---|---|
| 2,250 | 40 | 52 | 4,600 |
| 2,750 | 40 | 48 | 4,910 |
| 2,750 | 30 | 84 | 6,450 |
| 3,250 | 30 | 36 | 4,910 |
| 4,000 | 50 | 16 | 4,710 |
| 4,000 | 30 | 48 | 6,150 |
| 4,000 | 20 | 272 | 16,000 |

In interpreting Table I, it is apparent that at least a 40% weight concentration of the block polymer having a hydrophobic base of at least 2,250 molecular weight with at least about 52.0 moles of ethylene oxide condensed thereto will be necessary to form a ringing gel in an aqueous solution. In all cases, the block polymers above the minimums indicated in Table I will form gels in aqueous solutions up to 90 weight percent concentration and higher. Above 90 weight percent concentration, however, the gels tend to become indistinguishable from the starting block polymer itself. Therefore, the weight concentration is a preferred maximum at 90 weight percent. Thus, a (in the above Formula II) is an integer such that the hydrophobic base has a molecular weight of at least 2,250 and b is an integer from about 8 to 180 or higher. It is to be understood that the molecular weight of hydrophobic base may be other than those illustrated in Table I. Thus, for example, if a hydrophobic base of about 2,500 molecular weight is used, it is recognized that a gel may be formed from the block polymer at a concentration of 40 weight percent in an aqueous solution where about 50 moles of ethylene oxide are present in the block polymer.

The behavior of the block polymers in forming the gels in Formulas (I) and (II) is believed to be explained on the basis of hydrate formation. It may be speculated that the hydrophobe, because it is different from the hydrophobe of other types of non-ionics, may, in its own right, immobilize water independently of the oxyethylene chain by hydrogen bonding. It is noteworthy that gel formation occurs at about 70° F. to 80° F., even where the block polymer contains more than 200 moles of ethylene oxide or over 100 moles per block. It is also believed that the nature of the block polymer adds to this phenomena. It should be noted that the block polymer used in the gels of this invention exhibit a hydrophobe lying among four equal hydrophiles, whereas non-ionics commonly encountered, such as the oxyethylated fatty alcohols and alkyl phenols, have only one hydrophile. This difference in structure suggests that a loose micellar structure is obtained with this class of nonionics and that gel formation would more readily involve entrapment of free water in addition to water due to hydrogen bonding.

In any instance, the present compositions can include a detectable label, and the inclusion of a label would be especially helpful in instances where a surgeon is attempting to implant a certain amount of the composition in a given location. The label can be any non-toxic substance that is detectable by an imaging technique. For example, the present compositions can include a radio-opaque tag such as iodine, a fluorophore, or a metallic particle, such as gold micro- or nanoparticles, that can be detected by magnetic resonance imaging. The inclusion of a detectable label enables the compositions to be visualized both during and after the implantation procedure, and a combination of agents can be included. For example, the compositions can include a label that degrades for imaging in the short term and a more stable label for imaging in the long term. Fluorescent labels may be especially amenable to viewing during a procedure with a hand-held device. For example, the surgeon could detect any undesired flow of the composition from the intradiscal space or other target area. The methods of treating a patient who has a compromised spinal disc (described further below) can thus include a step of visualizing or imaging the composition.

Because of the thermoreversible nature of the present compositions, should a patient require it, the amount of material implanted can be adjusted in either direction; the volume of an implant may easily be adjusted upward by injecting additional material and downward by cooling and removing material by suction. As a result, the compressibility of the implant may be adjusted in response to changes in the status of the patient.

The molar mass of the poloxamer can vary, as can the content of polyoxyethylene. For example, the poloxamer can include about 30-90% polyoxyethylene (e.g., at least or about 70% polyoxyethylene or at least or about 35, 40, 45, 50, 55, 60, 65, 75, 80, or 85% polyoxyethylene).

In addition to being sterilized or sterilizable, the compositions can further contain an antimicrobial agent, such as an antibiotic, antiviral, or antifungal agent.

As the compositions are suitable for implantation, they may be manufactured and packaged with or within containers or other devices and paraphernalia useful for their implantation. For example, the compositions can be contained in a syringe or other hand-held vessel from which they can be extruded. Alternatively, the compositions can be contained in a vessel, such as an ampoule or stoppered container from which they can be withdrawn (e.g., aspirated through a needle). The container holding the composition (e.g., the syringe or ampoule) can be attached to or packaged with a needle for precisely delivering the composition to a region within a patient's body. Where percutaneous delivery is desired, the composition can be contained in or packaged with tubing (e.g., a catheter) suitable for insertion through the skin. The tubing would be supplied in a length sufficient to reach the target area of the patient's body, and tubing of variable length or multiple tubes of different lengths may be included for the surgeon's choice.

While the compositions may be included in the kits in ready-to-use forms, other kits of the invention may include two or more solutions that are mixed together prior to use. The two or more solutions can be contained in separate containers or they may be contained in separate compartments of a single container. In the latter case, the container may include one or more partitions that can be broken prior to use (e.g., by applying pressure to an external wall of the container), thereby allowing the solutions to mix. In another embodiment, the kits can include one or more solutions and one or more solid agents (e.g., a poloxamer in solid form) that are combined prior to use.

In addition, any of the kits can include a jacket or balloon for insertion into a target region (e.g., a prepared space for a spinal disc replacement) prior to filling the region with the composition. The jacket or balloon can be constructed from any physiologically acceptable material, including those that can expand to accommodate the composition. The jacket or balloon is preferably flexible and bioinert. It may be fashioned from a polymer or co-polymer (e.g., polyurethane) or it may be a bioceramic (e.g., an oxide ceramic or silica ceramic). Preferably, the material of the jacket or balloon (e.g., the bioceramic) will have a low Young's modulus to prevent cracking. As gelatinous foam can also be used around the periphery of an implant, such foam can be included in the kits. Finally, as the compositions of the invention vary in stiffness, the kit can include two compositions as described herein; a first composition that forms a stiffer gel, to be applied first around the periphery of the implant area, and a second composition that forms a more pliable gel, to be applied in the center of the implant area.

Any of the kits can also contain instructions in a suitable medium (e.g., in print, audio, video, or computer readable form). Each of the compositions described above as being suitable for inclusion in a kit as well as the kits per se are within the scope of the present invention.

Drug delivery devices comprising a biocompatible composition, as described herein, and methods of use are also within the scope of the invention and are described further below. When configured as a drug delivery device, the present compositions can be packaged as kits with instructions for use.

Treatment of Injured or Diseased Spinal Discs:

To achieve one of the objects of the present invention, a spinal disc nucleus pulposus implant is provided which comprises a biocompatible composition, as described herein. Due to the composition's properties, it can be injected into an intradiscal space in a fluid state where it will gel upon equilibrating with physiological temperatures. The change in phase from a liquid/injectable solution to a solid/gelled material is brought about by an increased temperature, and no other cross-linking or curing factor need be employed. Since the present compositions can be free of additive curing or cross-linking agents, even if some of the composition reaches the bloodstream, the patient is not endangered. Thus, the present compositions are biocompatible in the sense that they are non-toxic and/or exhibit tolerable side effects, and we expect the lack of curing or cross-linking agents to confer an added safety benefit.

The poloxamer within the composition may be one that is commercially available, such as Pluronic® F-127 or it may be a polymer having similar biocompatibility and gel point properties (e.g., similar to Pluronic® F-127). More generally, the various compositions described above are useful in spinal disc repair and treatment.

The biocompatible composition, which we may also refer to as a spinal disc nucleus pulposus implant, can be injected by essentially any injection device, including commonly used needles and syringes. Such delivery devices can be pre-loaded with the compositions for ease of use, and such pre-loaded devices are within the scope of the present invention; the invention features such pre-loaded devices per se as well as kits including them.

The biocompatible compositions can be injected in a cooled fluid state (e.g., at about 4° C. to about 20° C.) through an aperture in the natural annulus of a patient. The patient can be positioned in a supine position so that gravity facilitates the movement of the cooled, fluid composition downward and into the intradiscal space within the annulus. In addition, placing the patient in a supine position helps prevent the composition from flowing backward out of the aperture while it is still in a liquid/injectable form. The biocompatible compositions may also be implanted in the patient percutaneously, for example via a catheter, following a percutaneous discectomy. In that instance, the compositions may be injected into the intradiscal space via the same conduit through which the percutaneous discectomy is performed. The aperture into which the fluid is injected is typically caused by injury, but it may be created artificially.

Upon injection into the patient, the biocompatible compositions, as described herein, warm to physiological temperatures and thereby gel and conform to the shape of the spinal disc nucleus. The development of an appropriate shape may be assisted by the natural pressure the surrounding spine and natural tissue exerts on the material.

While positioning the patient in a supine position can impede extrusion of the compositions from an aperture in the annulus, the surgeon may also (or may alternatively) employ a one-way valve to impede extrusion or "backflow." Accordingly, the devices and kits of the invention that are designed for spinal disc repair can include a one-way valve that can be placed on or attached to the catheter or needle through which the compositions pass. The valve can be attached by the surgeon or it may be pre-assembled near the distal tip of the catheter or needle. To facilitate placement, the valve can be of a limited size (e.g., about 5-10 mm in diameter) and/or fashioned from transparent material. Instead of attaching the valve to the delivery device, it may be surgically positioned with an aperture in the annulus, and the cooled, fluid, compositions may be injected into the annulus through the valve. Regardless of the precise configuration, the valve can be removed from the aperture in the annulus once the composition is cured by warming. If necessary, the aperture in the annulus can be closed by welding with radiofrequency energy or by other known tissue welding techniques.

Significantly, the state of the present implants is reversible; the cured material in a gelled state may be returned to a fluid state by cooling, and it can then be removed from any confined area in which it has been placed (e.g., the area normally occupied by the nucleus pulposis). The ability to reverse the state of the compositions from a solid/gelled phase to a more liquid phase enables the surgeon to reduce the size of the implant if necessary (e.g., by inserting a cooled needle to remove some of the volume of the implant). Alternatively, a suitably small catheter with cooling capability or another form of a cooling probe or device can be inserted to cool the implant and enable its complete or partial removal. Any cooling device that includes a lumen can be used to both cool and remove or withdraw the composition (e.g., through the lumen of the catheter by suction). Conversely, if a patient experiences pain or further damage to the spinal disc nucleus, an additional amount of the composition can be injected into the nucleus to increase the volume of the implant. Additional material may also be injected to add to the implant to compensate for any degradation of the implant over time. As indicated, the present compositions can be completely removed and replaced if desired by cooling the material for removal as described above. This enables the implantation procedure to be entirely repeated. Thus, the present compositions can be readily modified both during implantation and subsequent to the initial implantation procedure to allow additional shaping or re-shaping and manipulation of the size and compressibility of the implant. Significantly, the modification of the implant may be performed percutaneously and on numerous occasions.

As described above, the present compositions can be injected in a cooled fluid state directly into the intradiscal space within the annulus of a patient. Alternatively, a jacket or balloon may first be inserted into the intradiscal space within the annulus of the patient. The compositions are then cured by heat (physiological temperatures). Where there is a jacket or balloon, the implant forms within it. Accordingly, the devices and kits of the invention that are designed for spinal disc repair can include a thin-walled, flexible, jacket or balloon of a size conforming approximately to the size of the nucleus pulposa. The jacket or balloon can be formed of any material suitable for surgical implantation, and may be elastic or substantially non-elastic. A jacket or balloon may also be formed in effect by first injecting a composition that becomes high rigid when cured and thereby forms a shell that is then filled with a composition that cures to a less rigid structure. This construction of the implant, with a more rigid shell encompassing a less rigid interior, may advantageously mimic a healthy disc nucleus. Providing a jacket, balloon, or shell to contain the material may also advantageously prevent the flow of the compositions into locations where they should not be present. For example, a jacket, balloon, or shell can impede the compositions from flowing out through any rupture or incision in the annulus through with the composition was inserted (or through any other rupture or open space). In another embodiment, a membrane of gelatinous foam can be coated on the walls of the intradiscal space to impede the outflow of the composition before it is cured by the body's heat. Accordingly, the devices and kits of the invention that are designed for spinal disc repair can include two compositions, one formulated to produce a more rigid structure upon curing and one formulated to produce a less rigid structure upon curing. Where a gelatinous foam is formed, the kit can include such a foam optionally contained within a delivery device such as a syringe. While packaging the present compositions within the device that will be used to deliver them has certain advantages (e.g., less susceptibility to contamination and ease of use for the surgeon, reducing the length of the operation), any of the compositions can be packaged in a vessel (e.g., an ampoule) from which they are removed to a delivery device.

Figure 1:
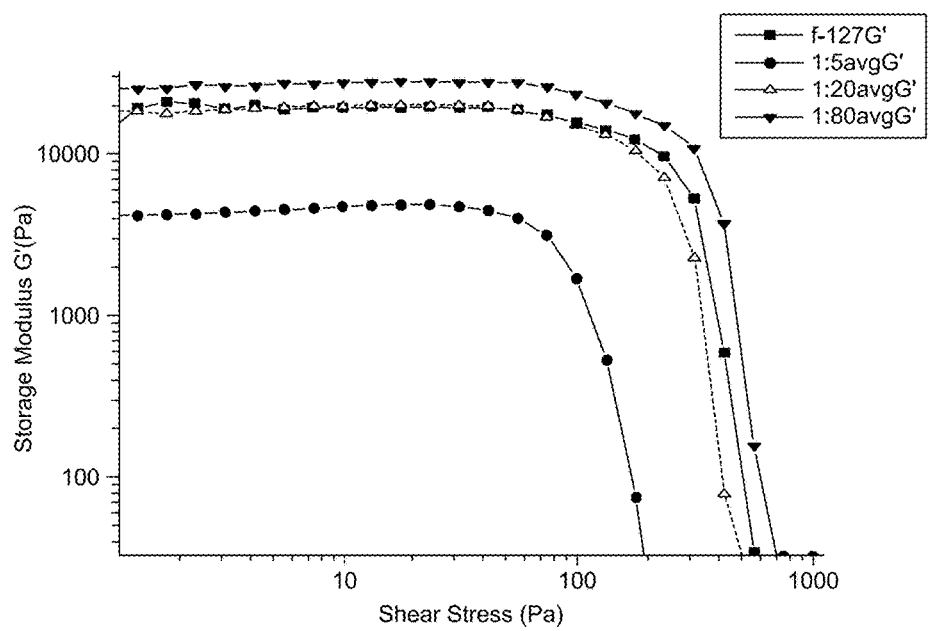
FIG. 1 is a line graph depicting rheology data gathered upon testing the hydrogels described in Example 1.

In one embodiment, the methods of the invention that are directed to treating a spinal disc injury in a patient (e.g., by implanting a spinal disc nucleus pulposus implant) can include the steps of removing nucleus pulposus tissue from one or more of the patient's spinal discs, thereby creating an implantation site (or intradiscal space), and providing a composition as described herein to the implantation site. The composition can be provided by percutaneous injection or by injection in an open surgical field. For example, the nucleus pulposus tissue can be removed percutaneously via a conduit (e.g. a catheter), and the biocompatible composition can be injected through the same conduit. As noted, the surgeon can inject a first biocompatible composition into the intradiscal space to form a shell defining a space within the intradiscal space and then inject a second biocompatible composition into the space defined by the first biocompatible composition. The first composition will have a higher viscosity than the second composition so that the implant is more rigid externally and less rigid internally. While the invention is not so limited, Example 1 and FIG. 1 provide data demonstrating the effect of varying the amounts of the poloxamer and one or more additives (e.g., hyaluronic acid) to vary the stiffness of the cured composition.

Alternatively, or in addition, the methods can include a step in which the surgeon applies a gelatinous foam to an interior surface of the intradiscal space before injecting the biocompatible composition(s). Both the rigid, external composition and the gelatinous foam can serve to inhibit movement of the biocompatible composition from the intradiscal space.

Any of the methods described herein for treating a spinal disc injury can include the use of an imaging system to monitor the placement of the biocompatible composition, which may include an agent detectable by an X-ray (e.g., a radiopaque agent) or other imaging technique (e.g., MRI). In one embodiment, the biocompatible composition can include a fluorescent marker, and the placement of the composition can be carried out under fluoroscopic observation.

As necessary in the opinion of the surgeon, the methods can include a step of adjusting the compressibility of the implant to accommodate changes in a patient's status. For example, the methods can include injecting additional biocompatible material into the intradiscal space or cooling and removing at least a portion of the biocompatible material (e.g., by suction). The implant can be entirely replaced, should replacement prove necessary over time.

Treatment of Other Conditions:

The biocompatible compositions of the present invention can be used in other surgical procedures as well. For example, the compositions can be used to fill gaps or cavities throughout the body. For example, the compositions can be used to fill cranial defects, sinus cavities, gaps or gashes in bone caused by trauma (whether accidental or incurred as a part of a surgical or dental procedure), or other internal spaces in the body. In cosmetic procedures, the compositions can be used with scaffolds to replace (wholly or partially) cartilaginous tissue, such as the tissue present in the pinna of the ear or on the tip of the nose. For example, the surgeon can position a prosthetic scaffold and contour and smooth the appearance of the scaffold as desired by applying a biocompatible composition as described herein. In another use, the compositions can be applied as a layer or film between tissues to inhibit, for example, the formation of adhesions following a surgical procedure. Accordingly, the invention encompasses methods of treating a patient as described here by applying an amount of the present compositions in a location and in an amount sufficient to improve a physical deficit in the tissue, to fill an unwanted gap, space, or cavity, or to inhibit the formation of surgical adhesions. For example, the invention features methods of inhibiting the formation of adhesions in a patient following a surgical procedure by applying (e.g., through a needle and syringe or other hand-held extrusion device) a biocompatible composition, as described herein, to an area where surgical adhesions are likely to form following a surgical procedure. The compositions may also be spread, for example, over tissue in the abdomen, by gauze or a surgical sponge. Any of these methods can include a step of identifying a patient in need of treatment.

While the methods of the invention and the uses of the present compositions are clearly applicable to human patients, the invention is not so limited. As the compositions should be relatively inexpensive to manufacture, veterinary applications are within the scope of the invention and expected to be practical.

Any of the inventive methods described above with respect to a patient should be understood to encompass "use" of the present compositions. For example, in another aspect, the invention features the use of a composition as described herein in the preparation of a medicament. For example, the invention features the use of a composition as described herein in the preparation of a medicament for spinal disc repair; for remodeling of tissue (e.g., the cartilaginous tissue of the nose); for replacing tissue (e.g., in the context of trauma or a dental procedure); for delivering a therapeutic agent; and for inhibiting the formation of adhesions.

Delivery of Therapeutic Agents:

As the present compositions gel at higher temperatures, including body temperature, they can be used to deliver a wide variety of therapeutic agents to a patient, and biocompatible compositions including a therapeutic agent are within the scope of the present invention. These agents include conventional "small molecule" drugs, including organic compounds. Other suitable agents include nucleic acids (e.g., plasmid constructs, oligonucleotides, including those that mediate RNAi and microRNAs) and proteins (e.g., peptide hormones, neurotransmitters, and antibodies). The biocompatible compositions described herein can also be used to deliver cells in either a non-modified or genetically-modified form. Cells suitable for inclusion include any type of stem cell or other progenitor cell that is less than fully differentiated (e.g., a mesenchymal stem cell, an adult stem cell, an embryonic stem cell, or a stem cell derived from blood, bone, or muscle). The kits of the invention can include biocompatible compositions containing a therapeutic agent packaged as described above (e.g., pre-combined or available in separate containers or compartments for combination by the surgeon at the time of use).

Cell and Tissue Culture Media:

The compositions of the present invention can also be used as a cell or tissue culture substrate or incorporated into cell and tissue culture media. Accordingly, the invention encompasses any of the biocompatible compositions described herein for use in cell or tissue culture and a culture medium comprising such biocompatible compositions. The compositions can be packaged for use as cell culture media, and may be provided in powdered, flake, or lyophilized form for rehydration prior to use. As noted, the compositions can be used without supplemental agents (i.e., they can consist of aqueous solutions of the poloxamer, HA, and gelatin and/or fibronectin). Alternatively, the compositions or components thereof (i.e., the poloxamer, HA, and gelatin and/or fibronectin) can be added to an aqueous tissue culture medium. Suitable media included Dulbecco's Modified Eagle's Medium (DMEM), RPMI Media 1640, minimum essential media (MEM), F-10 nutrient mixture, F-12 nutrient mixture, other media (e.g., Media 199, basal medium Eagle (BME), and CMRL) and modified media (e.g., DMEM/F-12 and improved MEM). Essentially any cell or tissue culture media can be supplemented with the present compositions or the components thereof. Methods of culturing cells or tissue in the present compositions or in media supplemented with the present compositions are within the scope of the present invention. For example, one can coat a tissue culture vessel (e.g., a plastic or glass tissue culture plate or flask) with a biocompatible composition as described herein (or provide a pre-coated vessel) and add, to the coated vessel, cells or tissues and tissue culture medium. One can then manipulate the culture in any way desired (e.g., by adding growth factors, therapeutic agents or putative therapeutic agents, microbial agents, or nucleic acid constructs). Thus, the present compositions can be used in drug screening, including high through put screens.

EXAMPLES

Example 1

In the work described below, we generated hydrogels that varied in stiffness by varying the ratio of hyaluronic acid (HA) to the poloxamer (Pluronic® F-127). We first generated a solution of 0.5% HA (w/v) and a solution of 20% poloxamer (w/v) and then mixed the solutions at three different ratios: 1:80, 1:20, and 1:5 HA:poloxamer (v:v). Rheological data, presented in FIG. 1, shows that the 1:80 mixture produced a hydrogel that is stiffer than that formed by the poloxamer alone; the 1:20 mixture produced a hydrogel of about the same stiffness as the poloxamer alone;

and the 1:5 mixture produced a hydrogel that is softer than the poloxamer alone. Thus, by varying the ratio (or the degree of cross-linking) between HA and the poloxamer, one can control its mechanical properties.

Example 2

Figure 2:
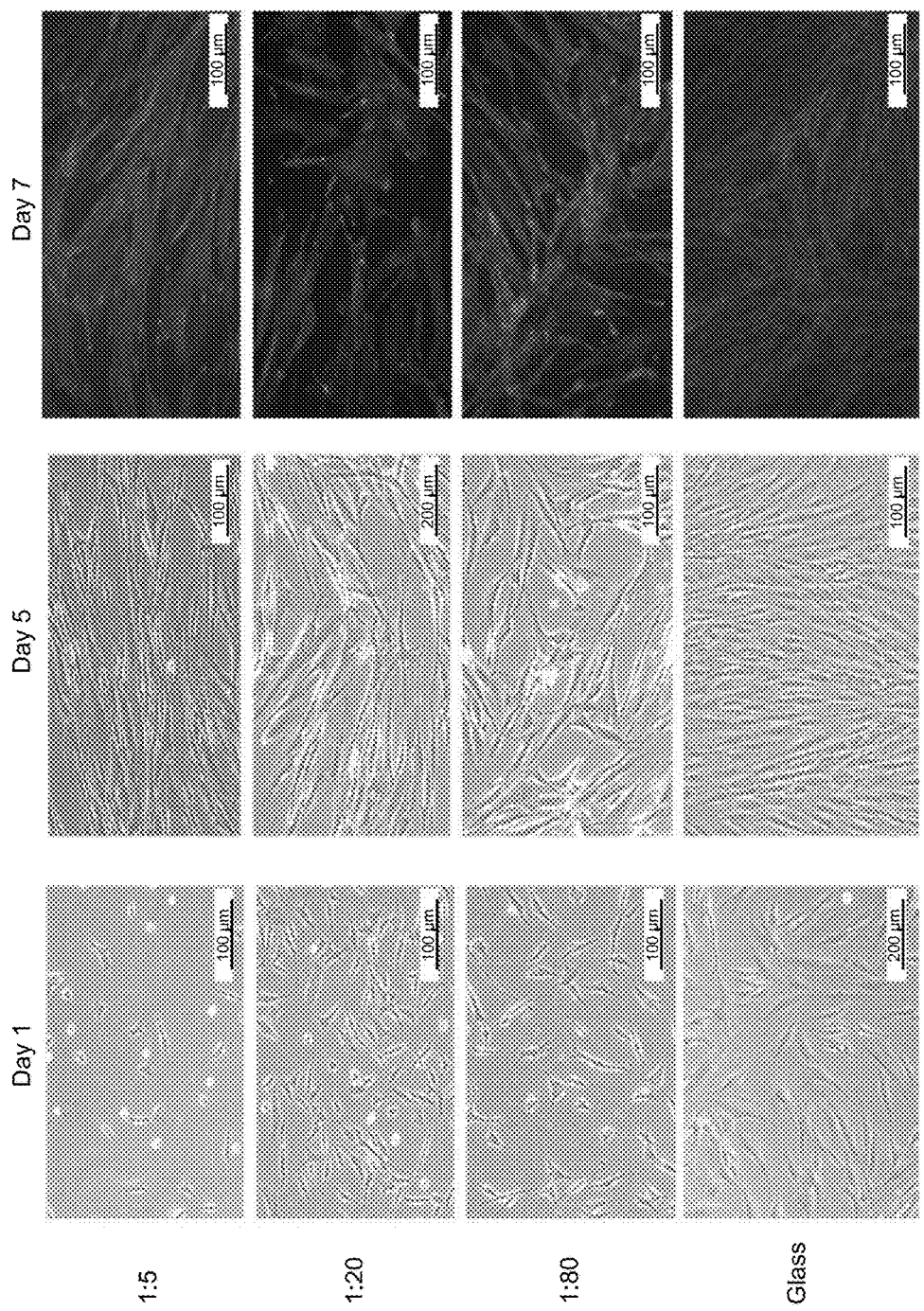
FIG. 2 is a panel of photomicrographs depicting fibroblasts grown on hydrogels containing or coated with varying amounts of gelatin, as described in Example 2, over time.

We plated CF-29 cells (adult human dermal fibroblasts) on poloxamer-based hydrogels containing different amounts of 0.5% HA and 0.5% gelatin (w/v) relative to the poloxamer Pluronic® F-127. The HA and gelatin were first mixed together at a ratio of 1:1 (v:v) and the resulting HA-gelatin solution was then mixed with the poloxamer solution were mixed at ratios of 1:5, 1:20, and 1:80 (HA-gelatin:poloxamer, v:v) and monitored them for seven days. To culture the cells, we first coated tissue culture plates with the HA-gelatin:poloxamer composition then added DMEM for about 12 hours before plating the cells. Cell number and morphology were observed relative to cell growth on a glass substrate. Photographs of the adherent cell cultures are shown in FIG. 2.

What is claimed is:

1. A biocompatible composition comprising 0.002-0.045% (w/v) of hyaluronic acid (HA), gelatin, and 18.182-39.604% (w/v) of a poloxamer, wherein the poloxamer has a hydrophobe base of polyoxy-propylene represented by $(C_3H_6O)$ and a formula:

$$HO(C_2H_4O)_b(C_3H_6O)_a(C_2H_4O)_bH \quad (II)$$

wherein a is an integer such that the hydrophobe base has a molecular weight of at least 2,250 and b is an integer from about 8 to 180 or more, wherein, when the hydrophobe has a molecular weight of 2,250 daltons, the gelatin contains at least 40% by weight of the block polymer and b is at least 26, and wherein, when the hydrophobe has a molecular weight of 4,000 daltons, the gelatin contains at least 20% by weight of the block polymer and b is at least 136.

2. The biocompatible composition of claim 1, wherein the composition is a liquid at 4° C. and a gel at 37° C.

3. The biocompatible composition of claim 1, wherein the polyoxy-propylene has a molar mass of about 1,000 to about 3,500 g/mol.

4. The biocompatible composition of claim 1, wherein the poloxamer contains about 30%-90% polyoxyethylene.

5. The biocompatible composition of claim 1, wherein the composition comprises hyaluronic acid and gelatin mixed in a ratio of about 1:1 (HA:gelatin, v:v).

6. The biocompatible composition of claim 5, wherein the composition comprises 0.002-0.045% (w/v) of the mixture of hyaluronic acid and gelatin and 27.273-29.703% (w/v) of the poloxamer.

7. The biocompatible composition of claim 1, wherein the composition is free from chemical cross-linking agents or wherein the poloxamer, hyaluronic acid (HA), and gelatin are not chemically cross-linked.

8. The biocompatible composition of claim 1, further comprising a detectable label.

9. The biocompatible composition of claim 1, further comprising a therapeutic agent.

10. The biocompatible composition of claim 9, wherein the therapeutic agent is an organic compound, nucleic acid, polypeptide, or biological cell.

11. A kit comprising the biocompatible composition of claim 1 and instructions for use.

12. A method of repairing a spinal disc, the method comprising:

(a) identifying a patient in need of treatment; and
(b) applying the biocompatible composition of claim 1 to the area of a damaged spinal disc.

13. A method of inhibiting the formation of adhesions in a patient following a surgical procedure, the method comprising:

(a) identifying a patient in need of treatment; and
(b) applying the biocompatible composition of claim 1 to an area where surgical adhesions are likely to form following a surgical procedure.

14. A biocompatible composition comprising 0.002-0.045% (w/v) of hyaluronic acid (HA), gelatin, or a mixture thereof and 18.182-39.604% (w/v) of a poloxamer, wherein the poloxamer comprises a hydrophobe of polyoxy-propylene represented by $(C_3H_6O)$ and a hydrophile of polyoxyethylene represented by $(C_2H_4O)$, and wherein the poloxamer has the following formula:

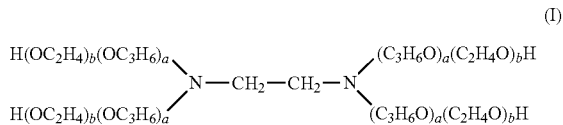

(I)

wherein a and b are integers representing the weight percent of the hydrophile (wpH-phile) and the molecular weight of the hydrophobe (mwH-phobe), respectively, wherein, when the a and b integers are plotted on a graph having an abscissa for the wpH-phile extending from 0 to 90 and an ordinate for the mwH-phobe extending from 501-8000, fall within four areas of the graph, a first area having values for a of between 10 and 90 wpH-phile and values for b of between 5501 and 8000 mwH-phobe, a second area having values for a of between 80 and 90 wpH-phile and values for b of between 2501 and 5501 mwH-phobe, a third area bounded on three sides by values for a of from 10 to 40 wpH-phile, values for b of from 2501 to 5501 mwH-phobe, and a first line connecting the a, b coordinates of 10 wpH-phile, 5501 mwH-phobe and 40 wpH-phile, 2501 mwH-phobe, and a fourth area bounded on three sides by values for a from 40 to 80 wpH-phile, values for b from 2001 to 2501 mwH-phobe, and a second line connecting the a, b coordinates of 40 wpH-phile, 2501 mwH-phobe and 80 wpH-phile, 2001 mwH-phobe, and wherein the polymers have (1) a hydrophobe molecular weight of from about 2,000 to about 8,000 daltons, (2) a hydrophile content of from 10% to 90% by weight of the biocompatible composition, and (3) a total molecular weight of from about 4,000 to 100,000 daltons.

15. The biocompatible composition of claim 14, wherein the composition is a liquid at 4° C. and a gel at 37° C.

16. The biocompatible composition of claim 14, wherein the poloxamer comprises polyoxy-propylene having a molar mass of about 1,000 to about 3,500 g/mol.

17. The biocompatible composition of claim 14, wherein the poloxamer contains about 30%-90% polyoxyethylene.

18. The biocompatible composition of claim 14, wherein the composition comprises hyaluronic acid and gelatin mixed in a ratio of about 1:1 (HA:gelatin, v:v).

19. The biocompatible composition of claim 18, wherein the composition comprises 0.002-0.045% (w/v) of the mixture of hyaluronic acid and gelatin and 27.273-29.703% (w/v) of the poloxamer.

* * * * *